US006696398B2

(12) United States Patent
Allen, Jr. et al.

(10) Patent No.: US 6,696,398 B2
(45) Date of Patent: Feb. 24, 2004

(54) STABILIZED COMPOSITION COMPRISING 2-(2-H-BENZOTRIAZOL-2-YL)-6-DODECYL-4-METHYLPHENOL

(75) Inventors: Aberdeen Allen, Jr., Union, NJ (US); Enrique Joel Valencia Garcia, Tacubaya (MX)

(73) Assignee: Colgate-Palmolive Company, New York, NY (US)

( * ) Notice: Subject to any disclaimer, the term of this patent is extended or adjusted under 35 U.S.C. 154(b) by 90 days.

(21) Appl. No.: 10/035,489

(22) Filed: Oct. 25, 2001

(65) Prior Publication Data

US 2003/0087779 A1 May 8, 2003

(51) Int. Cl.$^7$ .................................................. A61K 7/50

(52) U.S. Cl. ....................... 510/141; 510/147; 510/152; 510/445; 510/481; 510/499

(58) Field of Search ................................ 510/141, 147, 510/152, 445, 481, 499

(56) References Cited

U.S. PATENT DOCUMENTS 5,496,489 A 3/1996 Dussault et al. ............ 252/134

FOREIGN PATENT DOCUMENTS

| | | |
|---|---|---|
| WO | WO9744422 | 11/1997 |
| WO | WO9800505 | 8/1998 |
| WO | WO0063282 | 10/2000 |
| WO | WO0025730 | 11/2000 |
| WO | WO0109277 | 8/2001 |

OTHER PUBLICATIONS

Tinogard™ TL Liquid Benzotriazole UV Absorber; Ciba Specialty Chemicals Corporation.

*Primary Examiner*—Necholus Ogden
(74) *Attorney, Agent, or Firm*—Martin B. Barancik

(57) ABSTRACT

A solid translucent or transparent soap composition comprising a cleansing effective amount of soap and an antidiscoloration effective amount of the benzotriazole 2-(2H-benzotriazol-2-yl)-6-dodecl-4-methylphenol.

19 Claims, No Drawings

STABILIZED COMPOSITION COMPRISING 2-(2-H-BENZOTRIAZOL-2-YL)-6-DODECYL-4-METHYLPHENOL

BACKGROUND OF THE INVENTION

Soap-containing compositions generally need to be protected against decomposition as shown by discoloring, particularly yellowing, of the composition. Such protection usually comes from various opacifying materials present in a soap composition such as titanium dioxide, zinc oxide, and the like. However, certain solid soap-containing compositions are desirably translucent or even transparent. Opacifiers and other materials which bring about opaqueness and behave as discoloration inhibitors are absent from these compositions. Therefore, discoloration, particularly yellowing of the solid soap-containing compositions can be a significant issue. Such discoloration can become even more exacerbated when the container has at least one window through which the translucent or transparent soap bar can be visualized by the human eye, or the entire container is made from a material through which the translucent or transparent soap bar can be viewed.

Such discoloration of a transparent or translucent soap bar, particularly translucent, has now been essentially overcome through use of an antidiscoloring effective quantity of a specific benzotriazole namely 2-(2H-benzotriazol-2-yl)-6-dodecyl-4-methylphenol wherein the dodecyl is branched and/or linear with a CAS Number 23328-53-2/125304-04-3/104487-30-1 and INCI name of benzotriazolyl dodecyl p-cresol. It is available from Ciba Specialty Chemicals as Tinogard TL.

SUMMARY OF THE INVENTION

In accordance with the invention, there is a solid transparent or translucent cleansing composition comprising a cleansing effective amount of soap and an antidiscoloration effective amount of 2-(2H-benzotriazol-2-yl)-6-dodecyl-4-methylphenol.

DETAILED DESCRIPTION OF THE INVENTION

Soap is a long chain alkyl or alkenyl or mixture thereof carboxylate salt wherein the salt is generally alkali metal ammonium or ethanol ammonium such as triethanol ammonium. The long chain alkyl or alkenyl is about 8 to 20 carbon atoms in length counting the carbon of the carboxy group, preferably about 10 to about 18 carbon atoms. The quantity of soap present in the solid composition is at least about 1 wt. %, generally at least about 2, 5, 10, 20, 30, 40, 50, or 60 wt. % of the composition. Generally, the maximum quantity of soap is no more than about 70, 75 or 80 wt. % of the composition. Other surfactants can also be present in the composition, for example, synthetic anionic, amphoteric, nonionic and cationic surfactants, as long as the solid composition remains transparent or translucent. By translucent is meant a finite (non-zero) amount of visible light can be transmitted through the bar. Light transmittance can be measured using a UV-vis spectrophotometer. A one centimeter thick sample of the soap bar is prepared. The % transmittance of light, from 400–800 nm, through this sample is measured. In the opaque soaps, i.e., non-translucent, the transmittance of light through a one centimeter sample is zero. Transparent means 14 print font can be read through a bar sample that is one inch thick.

The specific benzotriazole effective in controlling discoloration in these soap-containing compositions is present in effective antidiscoloration amounts. Generally such quantities are at least about 0.01 wt. %, desirably at least about 0.03 wt. % and more desirably at least about 0.05 wt. % of the composition. The maximum amount of compound is dependent upon cost and the incidence of undesirable effects, though generally does not exceed about 0.25, desirably about 0.15 wt. % of the composition, and more desirably about 0.10 or about 0.075 wt. % of the composition.

The solid soap composition has no or essentially no opacifiers as previously mentioned. By opacifiers is meant compounds which limit the quantity of light passing through the solid composition. When opacifiers are present, the solid composition is generally opaque, i.e. "opacification". Examples of opacifiers include titanium dioxide, zinc oxide and the like.

The particular solid soap-containing compositions of this invention are desirably bar shaped. They are also at least translucent with respect to light. Such transmission of light through the solid bar is achieved by standard techniques primarily through the use of monohydric alcohol (ethanol) and, desirably, polyhydric substances such as glycerin, sorbitol, mannitol, xylitol, and propylene glycol mixtures thereof and the like. Desirable non-opaque compositions are those with a minimum of about 60 wt. % soap, and generally not more than about 75 wt.% soap, about 4 to about 19 wt. % of an alcohol or mixtures thereof, about 10 to about 25 wt. %, more desirably about 12 to about 20 wt. % water. Various adjuvants and other materials usually found such as preservatives, fragrance(s) and colorant(s) can be present as well. Also, not essentially present in the solid composition, preferably absent altogether are various polymer materials generally plastic such as polyester, polycarbonate, polyester polycarbonate, polyolefin, as well as various wood lacquers.

Other benzotriazoles are not compatible nor provide the desired stabilization. For example, Uvinul MS-40 from BASF, also known as benzophenone-4, CAS # 4065-45-6, changed the color of the bar during manufacturing. The desired benzotriazole must not only function as an effective discoloration inhibitor but also be safe for use, have ease of handling and be readily incorporated into the composition. Tinogard TL does not cause discoloration (yellowing of the bar). No special handling of this yellow liquid is required. The Tinogard TL is readily soluble into an organic system such as a fragrance.

The solid soap compositions are prepared in any manner well known in the art. The benzotriazole is solubilized in an organic material, for example, the fragrance, and added to the soap chips. The bars can be pressed from standard machinery.

The bars are then placed in standard containers or wraps, desirably those types that allow a user to visualize the bar. This can be done by having one or more windows on a solid container or a clear overwrap for the soap bar, preferably with a stiffener. The overwrap is generally a polyethylene terephthalate or a polyolefin. In like manner the see-through windows are of the same or similar plastics.

Below are examples of the invention. These examples are intended to illustrate the invention and not unduly limit it.

The subject benzotriazole (Tinogard TL) is solubilized in a fragrance and then added to the soap chips and thereafter preparing a translucent soap bar comprising the following composition and having 0.05 wt. % of the benzotriazole:

| COMPONENT | High Solubilizer (Wt. %) | Low Solubilizer (Wt. %) |
|---|---|---|
| Soap | 64–68 | 67–72 |
| Glycerin | 6–9 | 2–5 |
| Sorbitol | 4–7 | 2–5 |
| Free Fatty Acid | 1–5 | 1–5 |
| Propylene Glycol | 0–3 | 0–3 |
| Triethanolamine | 0.5–1.5 | 0–1 |
| Water | 12–20 | 12–20 |

A control bar is prepared in the same manner but with the benzotriazole Tinuvin 326. Typical colorants which can be employed include blue, peach, green, pink, and raspberry. The antioxidant is particularly useful for stabilization when a red colorant is present.

The bars (raspberry) are placed on a shelf in direct sunlight with no packaging, which allows light to pass through the bar. After 12 weeks aging, having the benzotriazole Tinuvin 326, the bars showed signs of yellowing (fading) as a result of exposure to direct sunlight. The bars with the Tinogard TL do not show any significant signs of yellowing. As well as visual evaluation, Colorimeter readings are also done on the raspberry bars after 13 weeks of aging in intense sunlight. Values for a and b indicate where the color is in the spectrum, i.e.,

| | |
|---|---|
| −a | green |
| +a | red |
| −b | blue |
| +b | yellow |

Thus, a decrease in a indicates a decrease in the red color, while a decrease in b indicate a decrease in the yellow hue.

The aging data are shown in the table below:

| 0.05 wt. % Benzotriazole | | a | b |
|---|---|---|---|
| Tinuvin 326 | Before aging | 11.46 | 4.65 |
| | After aging | 4.57 | 6.62 |
| | Change | −6.89 | 1.97 |
| | Yellowing | | |
| Tinogard TL | Before aging | 12.20 | −0.44 |
| | After aging | 11.33 | −1.89 |
| | Change | −0.87 | −1.45 |
| | No Yellowing | | |

The data show that with the addition of Tinuvin 326, the bars faded or became less red (low a values) after aging. The higher b value denotes yellowing. Upon the addition of Tinogard TL, the level of fading was decreased significantly (lower reduction in a). The lower b value denotes no yellowing.

What is claimed is:

1. A solid translucent or transparent soap composition comprising a cleansing effective amount of soap and an antidiscoloration effective amount of 2-(2H-benzotriazol-2-yl)-6-dodecyl-4-methylphenol wherein the dodecyl is branched and/or linear.

2. The composition in accordance with claim 1 wherein there is essentially no opacifier or mixture of opacifiers present in the composition.

3. The composition in accordance with claim 2 wherein the composition is in the shape of a bar.

4. The composition in accordance with claim 2 wherein the soap is at least about 1 wt. % of the composition.

5. The composition in accordance with claim 4 wherein there is about 19 wt. % of alcohol or mixtures thereof in the composition.

6. The composition in accordance with claim 5 wherein the composition is a bar which is in a container having at least one clear see-through window.

7. The composition in accordance with claim 5 wherein the composition is a bar packaged in a clear, see-through overwrap.

8. The composition in accordance with claim 2 wherein the composition is about 60 to 75 wt. % soap, about 4 to about 19 wt. % alcohol or mixtures thereof, and about 10 to about 25 wt. % water.

9. The composition in accordance with claim 8 wherein the alcohol comprises a mixture of glycerin and sorbitol.

10. The composition in accordance with claim 9 wherein the propylene glycol is also present.

11. The composition in accordance with claim 9 wherein triethanolamine is also present.

12. The composition in accordance with claim 10 wherein the triethanolamine is also present.

13. The composition in accordance with claim 1 wherein at least about 0.03 wt. % of the benzotriazole is present.

14. The composition in accordance with claim 7 wherein the composition is translucent.

15. The composition in accordance with claim 2 wherein the composition is translucent.

16. The composition in accordance with claim 3 wherein the composition is translucent.

17. The composition in accordance with claim 5 wherein the composition is translucent.

18. The composition in accordance with claim 14 wherein at least about 0.05 wt. % of the benzotriazole is present.

19. The composition in accordance with claim 18 wherein the composition has a red colorant therein.

* * * * *